(12) United States Patent
Arba-Mosquera

(10) Patent No.: US 11,883,330 B2
(45) Date of Patent: Jan. 30, 2024

(54) METHOD FOR CONTROLLING AN EYE SURGICAL LASER WITH A TRANSITION ZONE AT THE VOLUME BODY

(71) Applicant: Schwind eye-tech-solutions GmbH, Kleinostheim (DE)

(72) Inventor: Samuel Arba-Mosquera, Aschaffenburg (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 0 days.

(21) Appl. No.: 17/112,354

(22) Filed: Dec. 4, 2020

(65) Prior Publication Data
US 2021/0169693 A1    Jun. 10, 2021

(30) Foreign Application Priority Data
Dec. 6, 2019    (DE) ...................... 10 2019 133 428.4

(51) Int. Cl.
*A61F 9/008*    (2006.01)

(52) U.S. Cl.
CPC .. *A61F 9/0084* (2013.01); *A61F 2009/00846* (2013.01); *A61F 2009/00872* (2013.01); *A61F 2009/00897* (2013.01)

(58) Field of Classification Search
CPC .. A61F 2009/00846; A61F 2009/00872; A61F 2009/00897; A61F 9/0084
See application file for complete search history.

(56) References Cited

U.S. PATENT DOCUMENTS

| | | | |
|---|---|---|---|
| 9,937,033 B1 | 4/2018 | Peyman | |
| 2007/0161972 A1* | 7/2007 | Felberg | G16H 20/40 |
| | | | 606/4 |
| 2007/0282313 A1* | 12/2007 | Huang | A61B 3/1005 |
| | | | 606/5 |
| 2008/0319428 A1* | 12/2008 | Wiechmann | A61F 9/00838 |
| | | | 606/5 |

(Continued)

OTHER PUBLICATIONS

First Examination Report dated Sep. 18, 2020 in corresponding German Patent Application No. 10 2019 133 428.4.

*Primary Examiner* — Allen Porter
*Assistant Examiner* — Skylar Lindsey Christianson
(74) *Attorney, Agent, or Firm* — MEDLER FERRO WOODHOUSE & MILLS PLLC

(57) ABSTRACT

A method for controlling an eye surgical laser is disclosed for the separation of a volume body. The method includes determining a target position of a pupil relative to a laser beam and determining an optical zone with a treatment center on interfaces relative to an optical axis of the laser beam, determining a transition zone at the volume body as an extension of the interface, capturing a current actual position of the pupil, determining a deviation between the target position and the actual position, and decentering the determined optical zone relative to the optical axis depending on the determined deviation such that the edge of the volume body is generated concentrically to the optical axis and the optical zone is generated concentrically to the determined treatment center and within the transition zone. Further disclosed are a treatment apparatus, a computer program and computer-readable medium capable of performing the method.

26 Claims, 3 Drawing Sheets

(56) References Cited

U.S. PATENT DOCUMENTS

2015/0366711 A1\* 12/2015 Bischoff ............. A61F 9/00836
　　　　　　　　　　　　　　　　　　　　606/5
2018/0008461 A1\* 1/2018 Fu ....................... A61F 9/00827
2019/0060056 A1\* 2/2019 Serdarevic ............ A61F 2/1648

\* cited by examiner

METHOD FOR CONTROLLING AN EYE SURGICAL LASER WITH A TRANSITION ZONE AT THE VOLUME BODY

The invention relates to a method for controlling an eye surgical laser of a treatment apparatus for the separation of a volume body with an anterior interface and with a posterior interface, wherein the anterior interface and the posterior interface contact each other at an edge of the volume body, in particular from a human or animal cornea. Further, the invention relates to a treatment apparatus, to a computer program as well as to a computer-readable medium.

Opacities and scars within the cornea, which can arise by inflammations, injuries or congenital diseases, impair the sight. In particular in case that these pathological and/or unnaturally altered areas of the cornea are located in the axis of vision of the eye, clear sight is considerably disturbed. In known manner, the thus altered areas are eliminated by so-called phototherapeutic keratectomy (PTK) by means of an ablatively effective laser, for example an excimer laser. However, this is only possible if the pathological and/or unnaturally altered areas of the cornea are located in the superficial layers of the cornea. Subjacent areas, in particular within the stroma, are not reachable by means of ablative laser methods. Here, additional measures such as for example the exposure of the subjacent areas have to be taken by means of an additional corneal incision. By the additional measures, the treatment duration is disadvantageously considerably increased. In addition, there is the risk that further complications such as for example the occurrence of inflammations at the incision locations occur by the additional corneal incisions.

It is the object of the present invention to provide a method, a treatment apparatus, a computer program as well as a computer-readable medium, by means of which an improved control of an eye surgical laser can be performed.

This object is solved by a method, a treatment apparatus, a computer program as well as a computer-readable medium according to the independent claims. Advantageous forms of configuration are specified in the dependent claims.

An aspect of the invention relates to a method for controlling an eye surgical laser of a treatment apparatus for the separation of a volume body with an anterior interface and with a posterior interface, wherein the anterior interface and the posterior interface contact each other at an edge of the volume body, in particular from a human or animal cornea. Determining a target position of a pupil of the eye to a laser beam of the laser in a neutral pose of a beam deflection device of the treatment apparatus depending on patient information and determining an optical zone with a treatment center on at least one of the interfaces relative to an optical axis of the laser beam in the neutral pose of the beam deflection device depending on patient information are effected. A transition zone at the volume body is determined as an extension of the interface with the optical zone. A current actual position of the pupil is captured by means of the optical capturing device of the treatment apparatus. Determining a deviation between the target position and the actual position is effected. Decentration of the determined optical zone relative to the optical axis of the laser beam in the neutral pose of the beam deflection device is performed depending on the determined deviation such that the edge of the volume body is generated concentrically to the optical axis of the laser beam in the neutral pose of the beam deflection device and the optical zone is generated concentrically to the determined treatment center and within the transition zone.

In other words, if a deviation of the actual position from the target position should be present, it is provided that the volume body can nevertheless be reliably separated based on the transition zone and the treatment can be performed on the patient. In particular, this method can be performed, for example if a perfect centering of the eye should not have been accomplished. A new setup from the eye and from the laser, respectively, does not have to be performed, but the treatment can be continued based on the transition zone. Thus, a progression of the transition zone can in particular occur and an optical correction can nevertheless be realized at the correct location.

In other words, it is provided that a decentration of the optical zone of the volume body, which can also be referred to as lenticule, can be performed without displacement of the laser. However, the edge of the lenticule additionally remains concentric to the rotational axis of the beam deflection device, which can also be referred to as scanner. In particular, based on a difference vector between the actual position and the target position, the optical zone is applied within the lenticule. The optical zone becomes narrower in the direction of the decentration and wider in the opposite direction. Thus, an asymmetric transition zone can in particular be provided.

In particular, the beam deflection device has a neutral pose. For example, the beam deflection device can have two mirrors for deflecting the laser beam. Then, the neutral pose is given with a so-called 0/0 pose of the mirrors to each other. With a rotation of the mirrors, the incident laser beam experiences a deflection and thus can for example be positioned on the cornea. Thus, the beam deflection device has a rotational axis, around which the incident laser beam can be rotated depending on the mirror positions.

According to an advantageous form of configuration, the optical zone and transition zone are determined on the posterior interface. Alternatively or additionally, the optical zone and the transition zone can be determined on the anterior interface. Thereby, it is allowed that the transition zone can be formed on both interfaces. Thus, the control of the laser can in particular be effected such that a decentration can be performed and the optical zone can nevertheless be reliably generated concentrically to the determined treatment center within the transition zone.

It is also advantageous if the transition zone of the volume body is generated as an off-center crescent. In other words, the volume body is in particular lenticularly formed. Thereby, a reliable separation of the volume body can be realized.

It is further advantageous if the volume body is generated asymmetrically and concentrically to the optical axis of the laser beam in the neutral pose of the beam deflection device. Thereby, it is allowed that the optical zone is generated concentrically to the determined treatment center within the transition zone. Thereby, a treatment can be reliably performed even without reorientation of the laser.

It is further advantageous if the optical zone is decentered and/or displaced by a distance as the deviation between the target position and the actual position of the pupil. This deviation can in particular be referred to as difference vector. Thereby, the transition zone can be reliably determined based on the difference vector. Then, the difference vector is applied to the optical zone within the lenticule such that the transition zone becomes narrower in the direction of decentration and in particular wider in the opposite direction. Thereby, an asymmetric transition zone can in particular be provided.

Further, it has proven advantageous if the optical zone is decentered and/or displaced such that an asymmetric transition zone is generated. Based on the asymmetric transition zone, the optical zone can nevertheless be reliably generated concentrically to the determined treatment center within the transition zone. Thus, an improved treatment of the patient is allowed.

It is further advantageous if the control of the laser is effected such that topographic and/or tachymetric and/or morphologic data of the cornea is taken into account. Thus, topographic and/or tachymetric measurements of the cornea to be treated as well as of the type, the position and the extent of the for example pathological and/or unnaturally altered area within the stroma of the cornea can in particular be taken into account. In particular, control datasets are generated at least by providing topographic and/or tachymetric and/or morphologic data of the untreated cornea and providing topographic and/or tachymetric and/or morphologic data of the pathological and/or unnaturally altered area to be removed within the cornea.

A further aspect of the invention relates to a treatment apparatus with at least one surgical laser for the separation of a volume body with predefined interfaces of a human or animal eye for example by means of photodisruption and with at least one control device for the laser or lasers, which is formed to execute the steps of the method according to the preceding aspect. The treatment apparatus according to the invention allows that disadvantages arising in the use of usual ablative treatment apparatuses, namely relatively long treatment times and relatively high energy input by the laser into the cornea, are reliably avoided. These advantages are in particular achieved by the formation of the eye surgical laser as a photodisruptive laser.

Therein, the laser is suitable to emit laser pulses in a wavelength range between 300 nm and 1,400 nm, preferably between 700 nm and 1,200 nm, at a respective pulse duration between 1 fs and 1 ns, preferably between 10 fs and 10 ps, and a repetition frequency of greater than 10 kHz, preferably between 100 kHz and 100 MHz.

In an advantageous form of configuration of the treatment apparatus, the treatment apparatus comprises a storage device for at least temporarily storing at least one control dataset, wherein the control dataset or datasets include(s) control data for positioning and/or focusing individual laser pulses in the cornea, and includes at least one beam device for beam guidance and/or beam shaping and/or beam deflection and/or beam focusing of a laser beam of the laser. Therein, the mentioned control datasets are usually generated based on a measured topography and/or tachymetry and/or morphology of the cornea to be treated and the type of the pathologically and/or unnaturally altered area to be removed within the cornea.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including commands, which cause the treatment apparatus according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

The figures show the following.

In the figures, identical or functionally identical elements are provided with the same reference characters.

Figure 1:
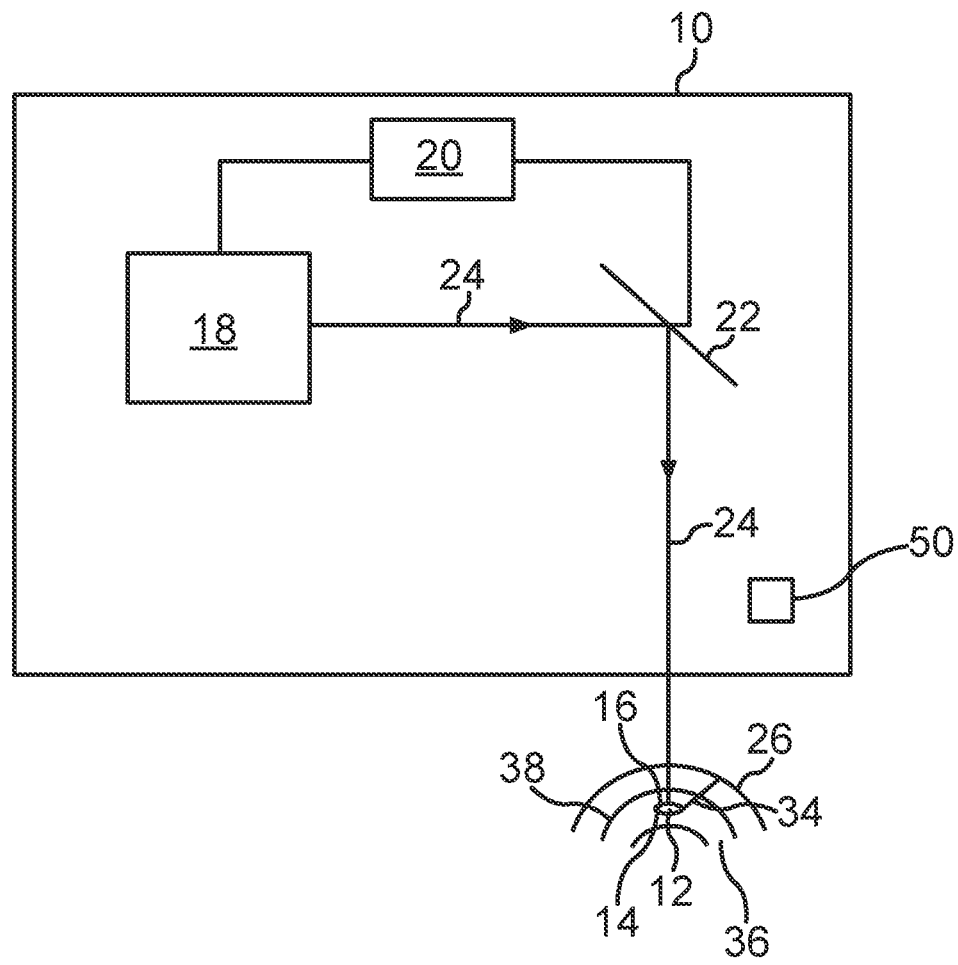
FIG. 1 is a schematic side view of an embodiment of a treatment apparatus.

FIG. 1 shows a schematic representation of a treatment apparatus 10 with an eye surgical laser 18 for the separation of a predefined corneal volume or volume body 12 with predefined interfaces 14, 16 of a cornea of a human or animal eye 40 (FIG. 3) by means of photodisruption as presently shown. One recognizes that a control device 20 for the laser 18 is formed besides the laser 18, such that it emits pulsed laser pulses in a predefined pattern into the cornea, wherein the interfaces 14, 16 of the volume body 12 to be separated are generated by the predefined pattern by means of photodisruption. In the illustrated embodiment, the interfaces 14, 16 form a lenticular volume body 12, wherein the position of the volume body 12 is selected in this embodiment such that a pathological and/or unnaturally altered area 32 (see FIG. 2) within a stroma 36 of the cornea is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam deflection device 22 such as for example a scanner. The beam deflection device 22 is also controlled by the control device 20 to generate the mentioned predefined pattern in the cornea. The beam deflection device 22 for example comprises two mirrors. The incident laser beam 24 can be rotated by rotation around a rotational axis. In a neutral pose of the mirrors, a so-called optical axis 30 (FIG. 3) of the laser beam 24 is in particular formed.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz.

In addition, the control device 20 comprises a storage device (not illustrated) for at least temporarily storing at least one control dataset, wherein the control dataset or datasets include(s) control data for positioning and/or for focusing individual laser pulses in the cornea. The position data and/or focusing data of the individual laser pulses are generated based on a previously measured topography and/or pachymetry and/or the morphology of the cornea and the pathological and/or unnaturally altered area 32 for example to be removed within the stroma 36 of the eye.

Figure 2:
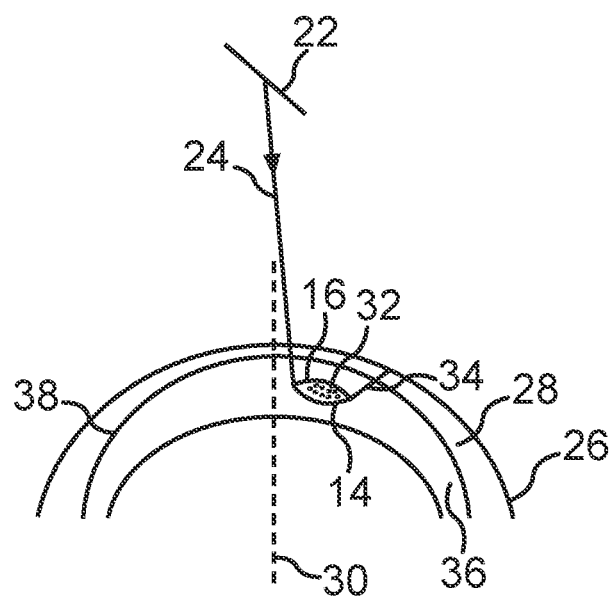
FIG. 2 is a further schematic side view of an embodiment of the treatment apparatus.

FIG. 2 shows a schematic diagram of the generation of the volume body 12 to be separated according to an embodiment of the present method. One recognizes that the interfaces 14, 16 are generated by means of the pulsed laser beam 24, which is directed towards the cornea or towards the surface 26 of the cornea via the beam deflection device 22. Therein, the interfaces 14, 16 form a lenticular volume body 12, which for example encloses the pathological and/or unnaturally altered area 32 within the stroma 36. Furthermore, the laser 18 generates a further incision 34 in the illustrated embodiment, which intersects the volume body 12 at a predefined angle and with a predefined geometry and is formed up to the surface 26 of the cornea. The volume body 12 defined by the interfaces 14, 16 can then be removed from the cornea via the incision 34. In the illustrated embodiment, the pathological and/or unnaturally altered area 32 is formed within the stroma 36.

In the illustrated embodiment, the interface 14, that is the interface located deeper in the eye or the stroma 36, is first formed by means of the laser beam 24, wherein it then corresponds to the posterior interface 14. This can be effected by at least partially circularly and/or spirally guiding the laser beam 24 according to the predefined pattern. Subsequently, the interface 16 is generated in comparable manner, which then corresponds to the anterior interface 16, such that the interfaces 14, 16 form the lenticular volume body 12 (see also FIG. 1). Subsequently, the incision 34 is also generated by the laser 18. However, the order of the generation of the interfaces 14, 16 and of the incision 34 can also be changed.

Figure 3:
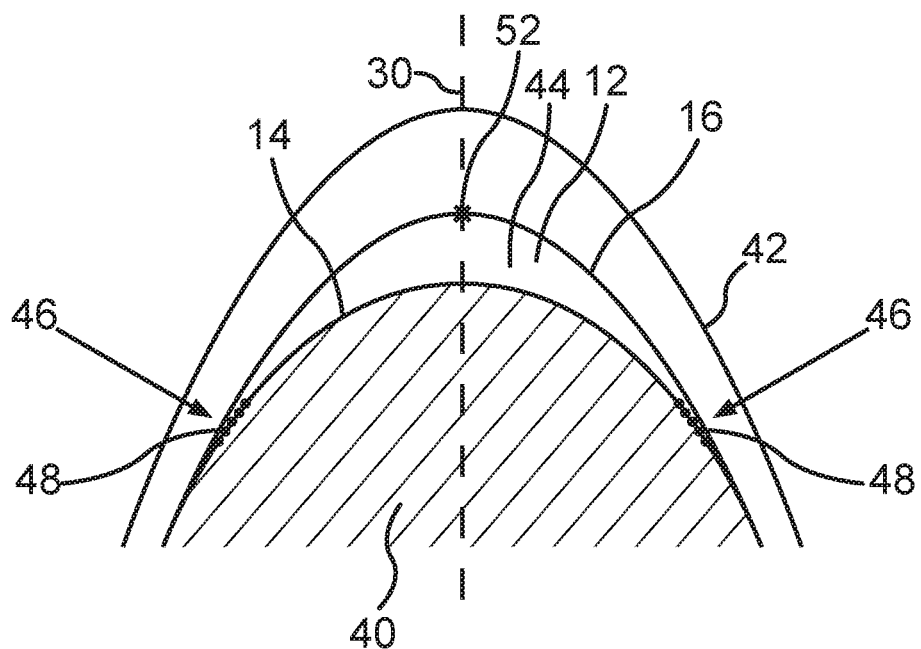
FIG. 3 is a schematic sectional view of an eye of a patient.

FIG. 3 shows an eye 40 of a patient in a first situation in a schematic sectional view. Presently, it can in particular be seen how a patient interface 42 of the treatment apparatus 10 rests on the eye 40. In particular, the volume body 12 is formed by the anterior interface 16 as well as by the posterior interface 14. In the present embodiment, the posterior interface 14 is to be regarded as an optical zone 44. At an edge 46 of the interfaces 14, 16, a transition zone 48 is in particular formed. In the present embodiment, the transition zone 48 is identically formed on both sides. In other words, the transition zone 48 is centered and symmetric.

Figure 4:
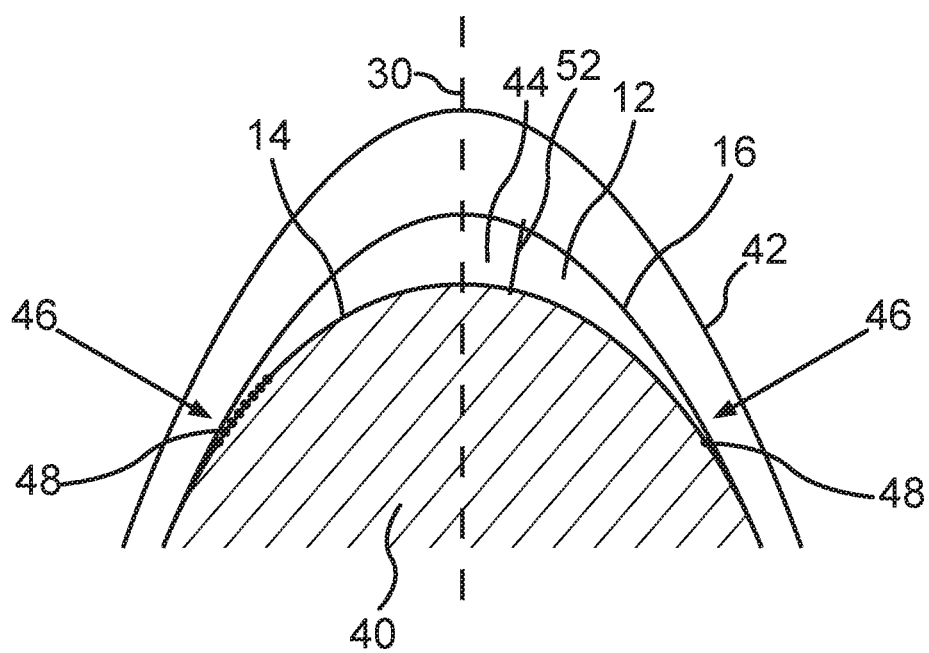
FIG. 4 is a further schematic sectional view of an eye of a patient.

FIG. 4 shows the eye 40 in a further situation in a schematic sectional view. In particular, a non-optimum eye position relative to the patient interface 42 is shown in FIG. 4 in contrast to FIG. 3.

In particular, it is shown in FIG. 4 that the anterior interface 16 and the posterior interface 14 contact each other at the edge 46 of the volume body 12. Determining a target position of a pupil of the eye 40 to the laser beam 24 in the neutral pose of the beam deflection device 22 depending on patient information and determining the optical zone 44 with a treatment center 52 on at least one of the interfaces 14, 16 relative to the optical axis 30 of the laser beam 24 depending on patient information can be performed. Determining the transition zone 48 at the volume body 12 as an extension of the interfaces 14, 16 with the optical zone 44 is effected. A current actual position of the pupil is captured by means of an optical capturing device 50 (FIG. 1) of the treatment apparatus 10. Further, a deviation between the target position and the actual position is determined and decentration of the determined optical zone 44 relative to the optical axis 30 of the laser 18 is effected depending on the determined deviation such that the edge 46 of the volume body 12 is generated concentrically to the optical axis 30 and the optical zone 44 is generated concentrically to the determined treatment center 52 and within the transition zone 48.

In particular, FIG. 4 shows that the optical zone 44 and the transition zone 48 can be determined on the posterior interface 14. Alternatively or additionally, the optical zone 44 and the transition zone 48 can also be determined on the anterior interface 16.

Figure 5:
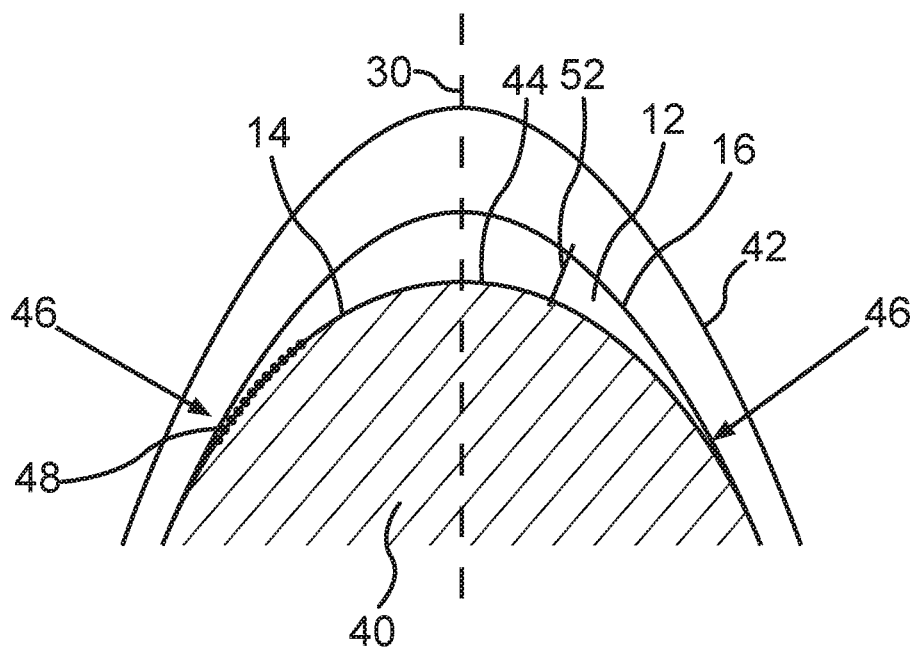
FIG. 5 is a still further schematic sectional view of an eye of a patient.

FIG. 5 shows an eye 40 of the patient in a further schematic sectional view. In FIG. 5, the treatment center 52 is in particular displaced such that the transition zone 48 is only formed on the left side shown in FIG. 5.

In particular, the transition zone 48 of the volume body 12 can be generated as an off-center crescent. Furthermore, it can in particular be provided that the volume body 12 is generated asymmetrically and concentrically to the optical axis 30. In particular, it can be provided that the optical zone 44 is decentered and/or displaced by a distance as the deviation between the target position and the actual position of the pupil. In particular, the optical zone 44 can be decentered and/or displaced such that an asymmetric transition zone 48 is generated.

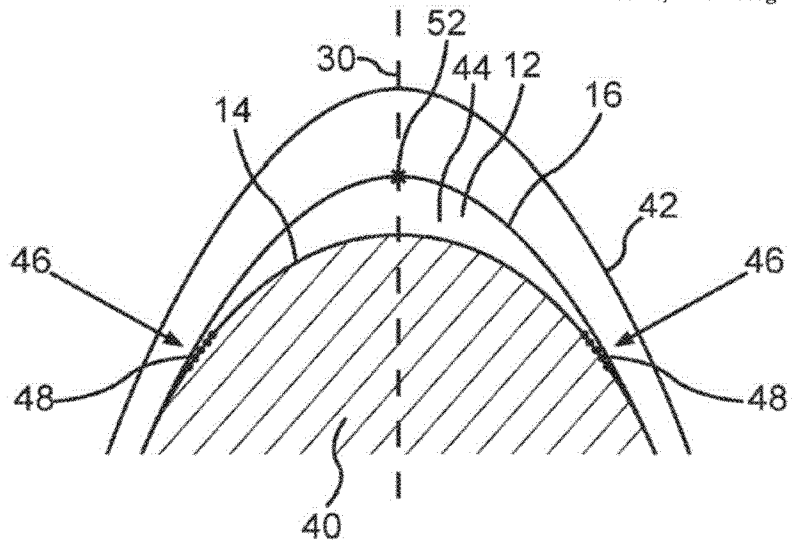

What is claimed is:

1. A method for controlling an eye surgical laser of a treatment apparatus for separation of a volume body with an anterior interface and with a posterior interface of an eye, wherein the anterior interface and the posterior interface contact each other at an edge of the volume body, comprising:
   determining a target position of a pupil of the eye relative to a laser beam of the laser in a neutral pose of a beam deflection device of the treatment apparatus depending on patient information;
   determining an optical zone with a treatment center on at least one of the anterior and posterior interfaces relative to an optical axis of the laser beam in the neutral pose of the beam deflection device depending on the patient information;
   determining a transition zone at the volume body as an extension of the posterior and/or anterior interface with the optical zone;
   capturing a current actual position of the pupil using an optical capturing device of the treatment apparatus;
   determining a deviation between the target position of the pupil and the actual position of the pupil;
   decentering the determined optical zone relative to the optical axis of the laser beam in the neutral pose of the beam deflection device, wherein the decentering is based on the determined deviation between the target position of the pupil and the determined actual position of the pupil such that after decentering,
   the treatment center of the optical zone is not axially aligned with the optical axis of the laser beam,
   the edge of the volume body is generated concentrically to the optical axis of the laser beam in the neutral pose of the beam deflection device, and the optical zone is generated concentrically to the determined treatment center and within the transition zone; and focusing the laser beam during or after the step of decentering the determined optical zone, wherein the transition zone of the volume body is generated as an off-center crescent relative to the determined treatment center and concentrical to the optical axis of the laser beam in the neutral pose of the beam deflection device, and the optical zone of the volume body is generated concentrical to the determined treatment center and off-center relative to the optical axis of the laser beam in the neutral pose of the beam deflection device.

2. The method according to claim 1, wherein the optical zone and the transition zone are determined on the posterior interface.

3. The method according to claim 1, wherein the optical zone and the transition zone are determined on the anterior interface.

4. The method according to claim 1, wherein the volume body is generated asymmetrically and concentrically to the optical axis of the laser beam in the neutral pose of the beam deflection device.

5. The method according to claim 1, wherein the optical zone is decentered and/or displaced by a distance of the deviation between the target position and the actual position of the pupil.

6. The method according to claim 1, wherein the optical zone is decentered and/or displaced such that an asymmetric transition zone is generated.

7. The method according to claim 1, wherein the control of the laser is effected such that topographic and/or pachymetric and/or morphologic data of a cornea is taken into account as the patient information.

8. The method according to claim 1, wherein the volume body is removed without reorientation of the laser beam from the neutral pose of the beam deflection device.

9. A treatment apparatus with at least one surgical laser for separation of a volume body with an anterior interface and with a posterior interface of a human or animal eye and with at least one control device for the laser or lasers, which is designed to execute the following method steps:

determining a target position of a pupil of the eye relative to a laser beam of the laser in a neutral pose of a beam deflection device of the treatment apparatus depending on patient information;

determining an optical zone with a treatment center on at least one of the anterior and posterior interfaces relative to an optical axis of the laser beam in the neutral pose of the beam deflection device depending on the patient information;

determining a transition zone at the volume body as an extension of the posterior and/or anterior interface with the optical zone;

capturing a current actual position of the pupil using an optical capturing device of the treatment apparatus;

determining a deviation between the target position of the pupil and the actual position of the pupil;

decentering the determined optical zone relative to the optical axis of the laser beam in the neutral pose of the beam deflection device, wherein the decentering is based on the determined deviation between the target position of the pupil and the determined actual position of the pupil such that after decentering, the treatment center of the optical zone is not axially aligned with the optical axis of the laser beam, an edge of the volume body is generated concentrically to the optical axis of the laser beam in the neutral pose of the beam deflection device, and the optical zone is generated concentrically to the determined treatment center and within the transition zone; and focusing the laser beam during or after the step of decentering the determined optical zone, wherein the transition zone of the volume body is generated as an off-center crescent relative to the determined treatment center and concentrical to the optical axis of the laser beam in the neutral pose of the beam deflection device and the optical zone of the volume body is generated concentrical to the determined treatment center and off-center relative to the optical axis of the laser beam in the neutral pose of the beam deflection device.

10. The treatment apparatus according to claim 9, wherein the optical zone and the transition zone are determined on the posterior interface.

11. The treatment apparatus according to claim 9, wherein the optical zone and the transition zone are determined on the anterior interface.

12. The treatment apparatus according to claim 9, wherein the volume body is generated asymmetrically and concentrically to the optical axis of the laser beam in the neutral pose of the beam deflection device.

13. The treatment apparatus according to claim 9, wherein the optical zone is decentered and/or displaced by a distance of the deviation between the target position and the actual position of the pupil.

14. The treatment apparatus according to claim 9, wherein the optical zone is decentered and/or displaced such that an asymmetric transition zone is generated.

15. The treatment apparatus according to claim 9, wherein the control of the laser is effected such that topographic and/or pachymetric and/or morphologic data of a cornea is taken into account as the patient information.

16. The treatment apparatus according to claim 9, wherein the at least one control device comprises at least one storage device for at least temporarily storing at least one control dataset, wherein the at least one control dataset includes control data for positioning and/or for focusing individual laser pulses in a cornea; and the treatment apparatus includes the beam deflection device for beam guidance and/or beam shaping and/or beam deflection and/or beam focusing of the laser beam of the laser.

17. A computer program including commands that causes the treatment apparatus according to claim 9 to execute the method steps recited therein.

18. The treatment apparatus according to claim 9, wherein the volume body is removed without reorientation of the laser beam from the neutral pose of the beam deflection device.

19. A non-transitory computer-readable medium having instructions stored thereon that, when executed by a processor, cause the processor to control an eye surgical laser of a treatment apparatus for separation of a volume body with an anterior interface and with a posterior interface of an eye, wherein the anterior interface and the posterior interface contact each other at an edge of the volume body, the processor:

determining a target position of a pupil of the eye relative to a laser beam of the laser in a neutral pose of a beam deflection device of the treatment apparatus depending on patient information;

determining an optical zone with a treatment center on at least one of the anterior and posterior interfaces relative to an optical axis of the laser beam in the neutral pose of the beam deflection device depending on the patient information;

determining a transition zone at the volume body as an extension of the posterior and/or anterior interface with the optical zone;

capturing a current actual position of the pupil using an optical capturing device of the treatment apparatus;

determining a deviation between the target position of the pupil and the actual position of the pupil;

decentering the determined optical zone relative to the optical axis of the laser beam in the neutral pose of the beam deflection device, wherein the decentering is based on the determined deviation between the target position of the pupil and the determined actual position of the pupil such that after decentering,
  the treatment center of the optical zone is not axially aligned with the optical axis of the laser beam,
  the edge of the volume body is generated concentrically to the optical axis of the laser beam in the neutral pose of the beam deflection device, and
  the optical zone is generated concentrically to the determined treatment center and within the transition zone; and focusing the laser beam during or after the step of decentering the determined optical zone, wherein the transition zone of the volume body is generated as an off-center crescent relative to the determined treatment center and concentrical to the optical axis of the laser beam in the neutral pose of the beam deflection device and the optical zone of the volume body is generated concentrical to the determined treatment center and off-center relative to the optical axis of the laser beam in the neutral pose of the beam deflection device.

20. The non-transitory computer-readable medium according to claim 19, wherein the optical zone and the transition zone are determined on the posterior interface.

21. The non-transitory computer-readable medium according to claim 19, wherein the optical zone and the transition zone are determined on the anterior interface.

22. The non-transitory computer-readable medium according to claim 19, wherein the volume body is generated asymmetrically and concentrically to the optical axis of the laser beam in the neutral pose of the beam deflection device.

23. The non-transitory computer-readable medium according to claim 19, wherein the optical zone is decentered and/or displaced by a distance of the deviation between the target position and the actual position of the pupil.

24. The non-transitory computer-readable medium according to claim 19, wherein the optical zone is decentered and/or displaced such that an asymmetric transition zone is generated.

25. The non-transitory computer-readable medium according to claim 19, wherein the control of the laser is effected such that topographic and/or pachymetric and/or morphologic data of a cornea is taken into account as the patient information.

26. The non-transitory computer-readable medium according to claim 19, wherein the volume body is removed without reorientation of the laser beam from the neutral pose of the beam deflection device.

\* \* \* \* \*

UNITED STATES PATENT AND TRADEMARK OFFICE
CERTIFICATE OF CORRECTION

PATENT NO. : 11,883,330 B2
APPLICATION NO. : 17/112354
DATED : January 30, 2024
INVENTOR(S) : Samuel Arba-Mosquera It is certified that error appears in the above-identified patent and that said Letters Patent is hereby corrected as shown below:

On the Title Page

Under item (57), "26 Claims, 3 Drawing Sheets" should read --25 Claims, 3 Drawing sheets-- as shown on the attached title page.

In the Claims

Column 8, Line 49-51: Please delete Claim 17.
Column 8, Line 52: Please renumber Claim 18 to Claim 17, dependent upon Claim 9.
Column 8, Line 56: Please renumber Claim 19 to Claim 18.
Column 10, Line 5: Please renumber Claim 20 to Claim 19, dependent upon Claim 18.
Column 10, Line 8: Please renumber Claim 21 to Claim 20, dependent upon Claim 18.
Column 10, Line 11: Please renumber Claim 22 to Claim 21, dependent upon Claim 18.
Column 10, Line 15: Please renumber Claim 23 to Claim 22, dependent upon Claim 18.
Column 10, Line 19: Please renumber Claim 24 to Claim 23, dependent upon Claim 18.
Column 10, Line 23: Please renumber Claim 25 to Claim 24, dependent upon Claim 18.
Column 10, Line 28: Please renumber Claim 26 to Claim 25, dependent upon Claim 18.

Signed and Sealed this
Twenty-first Day of May, 2024

Katherine Kelly Vidal
*Director of the United States Patent and Trademark Office*

(12) United States Patent
Arba-Mosquera

(10) Patent No.: US 11,883,330 B2
(45) Date of Patent: Jan. 30, 2024

(54) METHOD FOR CONTROLLING AN EYE SURGICAL LASER WITH A TRANSITION ZONE AT THE VOLUME BODY

(71) Applicant: Schwind eye-tech-solutions GmbH, Kleinostheim (DE)

(72) Inventor: Samuel Arba-Mosquera, Aschaffenburg (DE)

(73) Assignee: SCHWIND EYE-TECH-SOLUTIONS GMBH, Kleinostheim (DE)

(*) Notice: Subject to any disclaimer, the term of this patent is extended or adjusted under 35 U.S.C. 154(b) by 0 days.

(21) Appl. No.: 17/112,354

(22) Filed: Dec. 4, 2020

(65) Prior Publication Data
US 2021/0169693 A1   Jun. 10, 2021

(30) Foreign Application Priority Data
Dec. 6, 2019   (DE) .................... 10 2019 133 428.4

(51) Int. Cl.
*A61F 9/008*   (2006.01)

(52) U.S. Cl.
CPC .. *A61F 9/0084* (2013.01); *A61F 2009/00846* (2013.01); *A61F 2009/00872* (2013.01); *A61F 2009/00897* (2013.01)

(58) Field of Classification Search
CPC .. A61F 2009/00846; A61F 2009/00872; A61F 2009/00897; A61F 9/0084
See application file for complete search history.

(56) References Cited

U.S. PATENT DOCUMENTS

| | | | |
|---|---|---|---|
| 9,937,033 B1 | 4/2018 | Peyman | |
| 2007/0161972 A1* | 7/2007 | Felberg | G16H 20/40 606/4 |
| 2007/0282313 A1* | 12/2007 | Huang | A61B 3/1005 606/5 |
| 2008/0319428 A1* | 12/2008 | Wiechmann | A61F 9/00838 606/5 |

(Continued)

OTHER PUBLICATIONS

First Examination Report dated Sep. 18, 2020 in corresponding German Patent Application No. 10 2019 133 428.4.

*Primary Examiner* — Allen Porter
*Assistant Examiner* — Skylar Lindsey Christianson
(74) *Attorney, Agent, or Firm* — MEDLER FERRO WOODHOUSE & MILLS PLLC

(57) ABSTRACT

A method for controlling an eye surgical laser is disclosed for the separation of a volume body. The method includes determining a target position of a pupil relative to a laser beam and determining an optical zone with a treatment center on interfaces relative to an optical axis of the laser beam, determining a transition zone at the volume body as an extension of the interface, capturing a current actual position of the pupil, determining a deviation between the target position and the actual position, and decentering the determined optical zone relative to the optical axis depending on the determined deviation such that the edge of the volume body is generated concentrically to the optical axis and the optical zone is generated concentrically to the determined treatment center and within the transition zone. Further disclosed are a treatment apparatus, a computer program and computer-readable medium capable of performing the method.

25 Claims, 3 Drawing Sheets